US012773547B2

(12) United States Patent
Parks et al.

(10) Patent No.: US 12,773,547 B2
(45) Date of Patent: Oct. 27, 2026

(54) SYSTEMS AND METHODS FOR PUMP SPEED MODULATION

(71) Applicant: Abiomed, Inc., Danvers, MA (US)

(72) Inventors: Randi Parks, Danvers, MA (US); Jin Kwang Kim, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 241 days.

(21) Appl. No.: 18/481,479

(22) Filed: Oct. 5, 2023

(65) Prior Publication Data

US 2024/0115850 A1 Apr. 11, 2024

Related U.S. Application Data

(60) Provisional application No. 63/518,151, filed on Aug. 8, 2023, provisional application No. 63/436,255, filed on Dec. 30, 2022, provisional application No. 63/413,823, filed on Oct. 6, 2022.

(51) Int. Cl.

| | |
|---|---|
| ***A61M 1/10*** | (2006.01) |
| ***A61B 5/0215*** | (2006.01) |
| ***A61M 60/178*** | (2021.01) |
| ***A61M 60/515*** | (2021.01) |
| ***A61M 60/562*** | (2021.01) |
| ***G16H 40/63*** | (2018.01) |

(52) U.S. Cl.

CPC ........ *A61M 60/515* (2021.01); *A61M 60/178* (2021.01); *A61M 60/562* (2021.01); *G16H 40/63* (2018.01); *A61M 2205/04* (2013.01); *A61M 2205/3331* (2013.01); *A61M 2205/3365* (2013.01); *A61M 2206/10* (2013.01); *A61M 2230/005* (2013.01)

(58) Field of Classification Search

None

See application file for complete search history.

(56) References Cited

U.S. PATENT DOCUMENTS

| | | | | |
|---|---|---|---|---|
| 2004/0215050 A1 | 10/2004 | Morello | | |
| 2015/0141842 A1* | 5/2015 | Spanier | ............... | A61M 60/237 600/478 |
| 2018/0078159 A1 | 3/2018 | Edelman et al. | | |
| 2022/0016410 A1* | 1/2022 | Simundic | ............ | A61M 60/216 |

OTHER PUBLICATIONS

International Search Report and Written Opinion of the International Searching Authority for Application No. PCT/US2023/076064, dated Dec. 22, 2023.

* cited by examiner

*Primary Examiner* — Jon Eric C Morales

(74) *Attorney, Agent, or Firm* — Pierce Atwood LLP

(57) ABSTRACT

Methods and apparatus for controlling operation of a mechanical circulatory support (MCS) device to facilitate recovery of native heart function in a patient within which the MCS device is implanted are provided. The method includes controlling a pump of the MCS device to operate in first mode, obtaining one or more first cardiac values associated with the patient during operation of the MCS device, determining, based at least in part, on the obtained one or more first cardiac values to transition operation of the MCS device to a second mode, and controlling the pump of the MCS device to operate in the second mode when it is determined to transition operation of the MCS device to the second mode.

20 Claims, 7 Drawing Sheets

| | Decompression mode | Physiologic mode | Weaning mode |
|---|---|---|---|
| **Flow type** | Continuous | Pulsatile | Pulsatile/continuous |
| **Stimulus/clinical target** | LVEDV, LVEDD, LVEDP, Septum position | AoP, aortic wall tension, MAP 75-80 mmHg | Native CO or CI, Native Stroke volume, EF, etc. |
| **Aortic valves** | Closed most of the time | Open every ~5 cycles | Aortic valve open most of the time |
| **Goal** | Volume unloading/Maximum unloading | Allow physiological responses | Weaning |
| **Note** | Maximum unloading without suction | Sub modes:<br>1) Exercise mode (baroreceptor reset mode) - target MAP set > 75-80 mmHg, muscle oxygenation<br>2) Daily mode<br>3) Sleep mode | Speed decreases and observes clinical targets to initiate the next reduction in the speed |

FIG. 4

SYSTEMS AND METHODS FOR PUMP SPEED MODULATION

CROSS-REFERENCE TO RELATED APPLICATIONS

This application claims the benefit under 35 U.S.C. § 119(e) to U.S. Provisional Patent Application No. 63/413,823, filed Oct. 6, 2022, and titled, "SYSTEMS AND METHODS FOR PUMP SPEED MODULATION," and claims priority to U.S. Provisional Patent Application No. 63/436,255, filed Dec. 30, 2022, and titled, "SYSTEMS AND METHODS FOR PUMP SPEED MODULATION," and claims priority to U.S. Provisional Patent Application No. 63/518,151, filed Aug. 8, 2023, and titled, "SYSTEMS AND METHODS FOR PUMP SPEED MODULATION," the entire contents of each of which is incorporated by reference herein.

FIELD OF THE INVENTION

This disclosure relates to techniques for modulating pump speed of mechanical circulatory support device.

BACKGROUND

Fluid pumps, such as blood pumps, are used in the medical field in a wide range of applications and purposes. An intravascular blood pump is a pump that can be advanced through a patient's vasculature, i.e., veins and/or arteries, to a position in the patient's heart or elsewhere within the patient's circulatory system. For example, an intravascular blood pump may be inserted via a catheter and positioned to span a heart valve. The intravascular blood pump is typically disposed at the end of the catheter. Once in position, the pump may be used to assist the heart and pump blood through the circulatory system and, therefore, temporarily reduce workload on the patient's heart, such as to enable the heart to recover after a heart attack. An exemplary intravascular blood pump is available from ABIOMED, Inc., Danvers, MA under the tradename Impella® heart pump.

Such pumps can be positioned, for example, in a cardiac chamber, such as the left ventricle, to assist the heart. In this case, the blood pump may be inserted via a femoral artery by means of a hollow catheter and introduced up to and into the left ventricle of a patient's heart. From this position, the blood pump inlet draws in blood and the blood pump outlet expels the blood into the aorta. In this manner, the heart's function may be replaced or at least assisted by operation of the pump. Some devices associated with blood pumps inserted into the left ventricle to assist with heart function are also commonly referred to as left ventricular assist devices (LVADs). More generally, LVADs are an example of a type of mechanical circulatory support (MCS) device, also sometimes referred to as a "ventricular assist device/system," that may be used to support cardiac function in a patient.

An intravascular blood pump is typically connected to a heart pump controller that controls the heart pump, such as motor speed, and collects and displays operational data about the blood pump, such as heart signal level, battery temperature, blood flow rate, and plumbing integrity. An exemplary heart pump controller is available from ABIOMED, Inc. under the trade name Automated Impella Controller™. The controller may raise alarms when operational data values fall beyond predetermined values or ranges, for example if a leak, suction, and/or pump malfunction is detected. The controller may include a video display screen upon which is displayed a graphical user interface configured to display the operational data and/or alarms.

SUMMARY

Described herein are systems and methods for modulating the operation of a blood pump to facilitate heart recovery (e.g., halting or reversing cardiac remodeling that occurs in heart disease) during chronic use (e.g., from weeks to months to years) of the pump. The inventors have recognized and appreciated that by monitoring physiological and/or pump signals over time, the pump flow may be adapted to meet hemodynamic needs of the patient and facilitate cardiac recovery. In some embodiments, the heart pump may adapt pump flow by operating in and switching between various modes, either automatically or manually.

In some embodiments, a method of controlling operation of a mechanical circulatory support (MCS) device to facilitate recovery of native heart function in a patient within which the MCS device is implanted is provided. The method includes controlling a pump of the MCS device to operate in first mode, obtaining one or more first cardiac values associated with the patient during operation of the MCS device, determining, based at least in part, on the obtained one or more first cardiac values to transition operation of the MCS device to a second mode, and controlling the pump of the MCS device to operate in the second mode when it is determined to transition operation of the MCS device to the second mode.

In one aspect, the first mode is a decompression mode and the second mode is a physiologic mode. In another aspect, the first mode is a physiologic mode and the second mode is a sub-mode of the physiologic mode. In another aspect, the sub-mode of the physiologic mode comprises an exercise mode or a sleep mode. In another aspect, the first mode is a physiologic mode and the second mode is a weaning mode. In another aspect, the first mode includes first operating parameters configured to operate the pump with a first flow type, and the second mode includes second operating parameters configured to operate the pump with a second flow type different from the first flow type. In another aspect, the first flow type is continuous flow and the second flow type is a pulsatile flow. In another aspect, the first mode is a mode that provides optimized (e.g., maximum) unloading of a left ventricle of a heart of the patient based on physiological signals. In another aspect, the second mode is a mode that modulates a speed of the pump of the MCS device based on physiological responses of the patient. In another aspect, the second mode is a mode that facilitates reverse remodeling of heart function in the patient. In another aspect, optimized unloading of the left ventricle comprises maximum unloading of the left ventricle.

In another aspect, the method further comprises selecting a set of cardiac values to obtain based, at least in part, on the first mode, and obtaining one or more first cardiac values associated with the patient during operation of the MCS device comprises obtaining the one or more first cardiac values included in the set of cardiac values. In another aspect, the one or more first cardiac values include one or more values obtained from the pump of the MCS device. In another aspect, the one or more first cardiac values include one or more values obtained from one or more sensors external to the MCS device. In another aspect, the one or more first cardiac values include one or more values obtained indirectly from information associated with one or more sensors. In another aspect, the method further comprises processing, with at least one machine learning model, the information associated with the one or more sensors to obtain the one or more first cardiac values.

In another aspect, the one or more first cardiac values include one or more values obtained from the pump of the MCS device, one or more values obtained from one or more sensors external to the MCS device and one or more values obtained indirectly from information associated with one or more sensors associated with the MCS device and/or the one or more sensors external to the MCS device. In another aspect, the method further comprises determining, based at least in part, on the one or more first cardiac values to adjust a speed of the pump of the MCS device, and adjusting the speed of the pump of the MCS device when it is determined to adjust the speed of the pump and when it is not determined to transition operation of the MCS device to the second mode. In another aspect, the method further comprises obtaining one or more second cardiac values associated with the patient during operation of the MCS device in the second mode, determining, based at least in part, on the obtained one or more second cardiac values to transition operation of the MCS device to a third mode, and controlling the pump of the MCS device to operate in the third mode when it is determined to transition operation of the MCS device to the third mode. In another aspect, the first mode is a decompression mode, the second mode is a physiologic mode and the third mode is a weaning mode. In another aspect, the first mode is a decompression mode, the second mode is a physiologic mode, and the third mode is a physiologic mode. In another aspect, the method further comprises selecting a set of cardiac values to obtain based, at least in part, on the second mode, and obtaining one or more second cardiac values associated with the patient during operation of the MCS device in the second mode comprises obtaining the one or more second cardiac values included in the set of cardiac values. In another aspect, the MCS device is a left ventricular assist device (LVAD). In another aspect, the first mode is a decompression mode and the second mode is a weaning mode. In another aspect, the method further includes receiving via a user interface, an instruction to transition operation of the MCS device to the second mode, and controlling the pump to operate in the second mode is performed in response to receiving the instruction.

In some embodiments, a controller for a pump of a mechanical circulatory support (MCS) device is provided. The controller includes at least one hardware processor configured to control a pump of the MCS device to operate in first mode, obtain one or more first cardiac values associated with the patient during operation of the MCS device, determine, based at least in part, on the obtained one or more first cardiac values to transition operation of the MCS device to a second mode, and control the pump of the MCS device to operate in the second mode when it is determined to transition operation of the MCS device to the second mode.

In one aspect, the first mode is a decompression mode and the second mode is a physiologic mode. In another aspect, the first mode is a physiologic mode and the second mode is a sub-mode of the physiologic mode. In another aspect, the sub-mode of the physiologic mode comprises an exercise mode or a sleep mode. In another aspect, the first mode is a physiologic mode and the second mode is a weaning mode. In another aspect, the first mode includes first operating parameters configured to operate the pump with a first flow type, and the second mode includes second operating parameters configured to operate the pump with a second flow type different from the first flow type. In another aspect, the first flow type is continuous flow and the second flow type is a pulsatile flow. In another aspect, the first mode is a mode that provides optimized (e.g., maximum) unloading of a left ventricle of a heart of the patient based on physiological signals. In another aspect, the second mode is a mode that modulates a speed of the pump of the MCS device based on physiological responses of the patient. In another aspect, the second mode is a mode that facilitates reverse remodeling of heart function in the patient. In another aspect, optimized unloading of the left ventricle comprises maximum unloading of the left ventricle.

In another aspect, the at least one hardware processor is further configured to select a set of cardiac values to obtain based, at least in part, on the first mode, and obtaining one or more first cardiac values associated with the patient during operation of the MCS device comprises obtaining the one or more first cardiac values included in the set of cardiac values. In another aspect, the one or more first cardiac values include one or more values obtained from the pump of the MCS device. In another aspect, the one or more first cardiac values include one or more values obtained from one or more sensors external to the MCS device. In another aspect, the one or more first cardiac values include one or more values obtained indirectly from information associated with one or more sensors. In another aspect, the at least one hardware processor is further configured to process, with at least one machine learning model, the information associated with the one or more sensors to obtain the one or more first cardiac values.

In another aspect, the one or more first cardiac values include one or more values obtained from the pump of the MCS device, one or more values obtained from one or more sensors external to the MCS device and one or more values obtained indirectly from information associated with one or more sensors associated with the MCS device and/or the one or more sensors external to the MCS device. In another aspect, the at least one hardware processor is further configured to determine, based at least in part, on the one or more first cardiac values to adjust a speed of the pump of the MCS device, and adjust the speed of the pump of the MCS device when it is determined to adjust the speed of the pump and when it is not determined to transition operation of the MCS device to the second mode. In another aspect, the at least one hardware processor is further configured to obtain one or more second cardiac values associated with the patient during operation of the MCS device in the second mode, determine, based at least in part, on the obtained one or more second cardiac values to transition operation of the MCS device to a third mode, and control the pump of the MCS device to operate in the third mode when it is determined to transition operation of the MCS device to the third mode. In another aspect, the first mode is a decompression mode, the second mode is a physiologic mode and the third mode is a weaning mode. In another aspect, the first mode is a decompression mode, the second mode is a physiologic mode, and the third mode is a physiologic mode. In another aspect, the at least one hardware processor is further configured to select a set of cardiac values to obtain based, at least in part, on the second mode, and obtaining one or more second cardiac values associated with the patient during operation of the MCS device in the second mode comprises obtaining the one or more second cardiac values included in the set of cardiac values. In another aspect, the MCS device is a left ventricular assist device (LVAD). In another aspect, the first mode is a decompression mode and the second mode is a weaning mode. In another aspect, the at least one hardware processor is further configured to receive via a user interface, an instruction to transition operation of the MCS device to the second mode, and controlling the pump to operate in the second mode is performed in response to receiving the instruction.

In some embodiments, a mechanical circulatory support (MCS) device is provided. The MCS device includes a pump, and a controller coupled to the pump, the controller comprising at least one hardware processor. The at least one hardware processor is configured to control the pump to operate in first mode, obtain one or more first cardiac values associated with the patient during operation of the MCS device, determine, based at least in part, on the obtained one or more first cardiac values to transition operation of the MCS device to a second mode, and control the pump to operate in the second mode when it is determined to transition operation of the MCS device to the second mode.

In one aspect, the first mode is a decompression mode and the second mode is a physiologic mode. In another aspect, the first mode is a physiologic mode and the second mode is a sub-mode of the physiologic mode. In another aspect, the sub-mode of the physiologic mode comprises an exercise mode or a sleep mode. In another aspect, the first mode is a physiologic mode and the second mode is a weaning mode. In another aspect, the first mode includes first operating parameters configured to operate the pump with a first flow type, and the second mode includes second operating parameters configured to operate the pump with a second flow type different from the first flow type. In another aspect, the first flow type is continuous flow and the second flow type is a pulsatile flow. In another aspect, the first mode is a mode that provides optimized (e.g., maximum) unloading of a left ventricle of a heart of the patient based on physiological signals. In another aspect, the second mode is a mode that modulates a speed of the pump of the MCS device based on physiological responses of the patient. In another aspect, the second mode is a mode that facilitates reverse remodeling of heart function in the patient. In another aspect, optimized unloading of the left ventricle comprises maximum unloading of the left ventricle.

In another aspect, the at least one hardware processor is further configured to select a set of cardiac values to obtain based, at least in part, on the first mode, and obtaining one or more first cardiac values associated with the patient during operation of the MCS device comprises obtaining the one or more first cardiac values included in the set of cardiac values. In another aspect, the one or more first cardiac values include one or more values obtained from the pump of the MCS device. In another aspect, the one or more first cardiac values include one or more values obtained from one or more sensors external to the MCS device. In another aspect, the one or more first cardiac values include one or more values obtained indirectly from information associated with one or more sensors. In another aspect, the at least one hardware processor is further configured to process, with at least one machine learning model, the information associated with the one or more sensors to obtain the one or more first cardiac values.

In another aspect, the one or more first cardiac values include one or more values obtained from the pump of the MCS device, one or more values obtained from one or more sensors external to the MCS device and one or more values obtained indirectly from information associated with one or more sensors associated with the MCS device and/or the one or more sensors external to the MCS device. In another aspect, the at least one hardware processor is further configured to determine, based at least in part, on the one or more first cardiac values to adjust a speed of the pump of the MCS device, and adjust the speed of the pump of the MCS device when it is determined to adjust the speed of the pump and when it is not determined to transition operation of the MCS device to the second mode. In another aspect, the at least one hardware processor is further configured to obtain one or more second cardiac values associated with the patient during operation of the MCS device in the second mode, determine, based at least in part, on the obtained one or more second cardiac values to transition operation of the MCS device to a third mode, and control the pump of the MCS device to operate in the third mode when it is determined to transition operation of the MCS device to the third mode. In another aspect, the first mode is a decompression mode, the second mode is a physiologic mode and the third mode is a weaning mode. In another aspect, the first mode is a decompression mode, the second mode is a physiologic mode, and the third mode is a physiologic mode. In another aspect, the at least one hardware processor is further configured to select a set of cardiac values to obtain based, at least in part, on the second mode, and obtaining one or more second cardiac values associated with the patient during operation of the MCS device in the second mode comprises obtaining the one or more second cardiac values included in the set of cardiac values. In another aspect, the MCS device is a left ventricular assist device (LVAD). In another aspect, the first mode is a decompression mode and the second mode is a weaning mode. In another aspect, the at least one hardware processor is further configured to receive via a user interface, an instruction to transition operation of the MCS device to the second mode, and controlling the pump to operate in the second mode is performed in response to receiving the instruction.

BRIEF DESCRIPTION OF DRAWINGS

FIG. 4 illustrates a chart of exemplary modes for operating a pump system of a mechanical circulatory support (MCS) device in accordance with some embodiments of the present technology.

DETAILED DESCRIPTION

Patients with chronic heart failure (CHF) currently have no reliable options to facilitate native heart recovery. Many late-stage CHF patients receive a durable mechanical circulatory support (MCS) device (e.g., a left ventricular assist device (LVAD)), but few recover from the disease while supported with the MCS device. One reason such patients may not recover is that conventional MCS devices are typically designed to meet the physiological demands of a patient in an acute setting rather than being designed to facilitate native heart recovery over longer durations of support. For instance, MCS devices used for long-term support are typically set to one speed for the duration of the support. Accordingly, the inventors have appreciated the benefit of modulating pump speed of the pump system during support with the MCS device. For example, some embodiments of the technology described herein are configured to track cardiac function over the duration of MCS device support and modulate operation of the device to meet physiological demand and/or to place the device in a particular mode/module depending on a phase of treatment/recovery that the patient is currently in (e.g., initial, recovery, exercise, weaning, etc.) to facilitate native heart recovery.

Figure 1A:
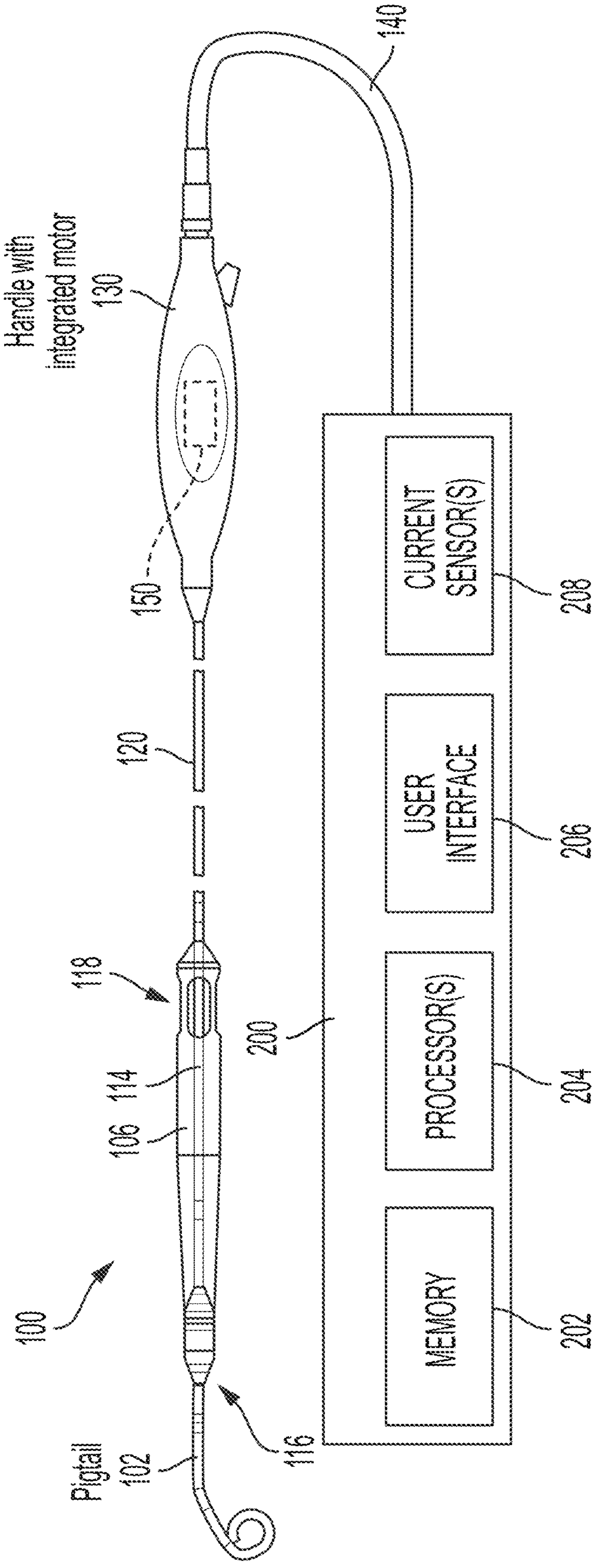
FIG. 1A illustrates a pump system in accordance with some embodiments of the present technology.
Figure 1B:
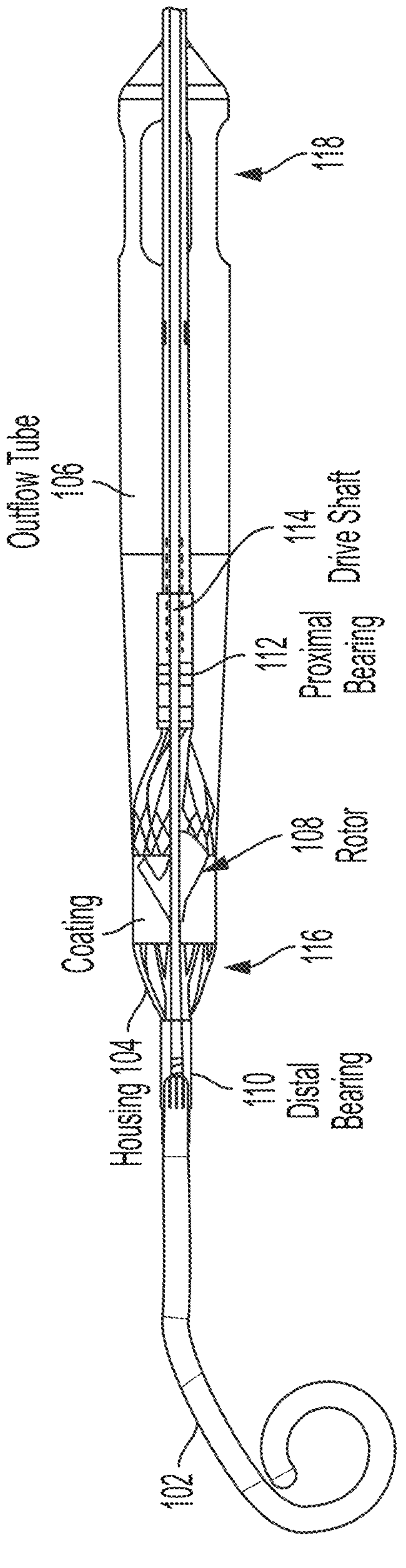
FIG. 1B is a cross-sectional view of a portion of the pump system of FIG. 1A.

Turning now to the figures, a pump system 100 (e.g., a portion of an MCS device) for use with some embodiments of the present technology is shown in FIGS. 1A and 1B. As shown, pump system 100 may be coupled to a control unit 200. Pump 100 may include a distal atraumatic tip 102, a pump housing 104 surrounding a rotor 108, an outflow tube 106, distal bearing 110, proximal bearing 112, inlet 116, outlet 118, catheter 120, handle 130, cable 140, and motor 150. As will be appreciated, although shown with an atraumatic tip, in some embodiments, the pump may not include such a tip. Pump housing 104 may be configured as a frame structure formed by a mesh with openings which may, at least in part, be covered by an elastic material. A proximal portion of pump housing 104 may extend into and be mounted in the hollow interior of outflow tube 106, and a distal portion of pump housing 104 may extend distally beyond the distal end of outflow tube 106. The exposed openings in the pump housing 104 extending distally beyond outflow tube 106 may form the inlet 116 of pump 100. The proximal end of outflow tube 106 may include a plurality of openings that form the outlet 118 of pump 100. Rotor 108 may be rotationally mounted between distal bearing 110 and proximal bearing 112, and may be coupled to a distal end of drive shaft 114. Drive shaft 114 may be flexible and may extend through catheter 120, through the hollow interior of outflow tube 106, into handle 130 and is coupled to motor 150, which is housed in handle 130. The proximal end of handle 130 may be coupled via cable 140 to control unit 200. A fluid may be circulated through the catheter 120 proximate to the drive shaft 114 and in the space surrounding the distal bearing 110 and proximal bearing 112 to lubricate those components and reduce friction during operation of the pump 100.

Control unit 200 may include one or more memory 202, one or more processors 204, a user interface 206, and one or more sensors, such as current sensors 208. Processor(s) 204 may comprise one or more microcontrollers, one or more microprocessors, one or more application specific integrated circuits (ASICs), one or more digital signal processors, program memory, or other computing components. Processor(s) 204 may be communicatively coupled to the other components (e.g., memory 202, user interface 206, current sensor(s) 208) of control unit 200 and may be configured to control one or more operations of pump 100. As a non-limiting example, control unit 200 may be implemented as an Automated Impella Controller™ from ABIOMED, Inc., Danvers, MA. In some aspects, memory 202 is included as a portion of processor(s) 204 rather than being provided as a separate component.

During operation, processor(s) 204 may be configured to control the electrical power delivered to motor 150 (e.g., by controlling a power supply (not shown)) by a power supply line (not shown) in cable 140, thereby controlling the speed of the motor 150. Current sensor(s) 208 may be configured to sense motor current associated with an operating state of the motor 150, and processor(s) 204 may be configured to receive the output of current sensor(s) 208 as a motor current signal. Processor(s) 204 may further be configured to determine a flow through the pump 100 based, at least in part, on the motor current signal and the motor speed, as described in more detail below. Current sensor(s) 208 may be included in control unit 200 or may be located along any portion of the power supply line in cable 140. Additionally or alternatively, current sensor(s) 208 may be included in motor 150 and processor(s) 204 may be configured to receive the motor current signal via a data line (not shown) in cable 140 coupled to processor(s) 204 and motor 150.

Memory 202 may be configured to store computer-readable instructions and other information for various functions of the components of control unit 200. In one aspect, memory 202 includes volatile and/or non-volatile memory, such as, an electrically erasable programmable read-only memory (EEPROM).

User interface 206 may be configured to receive user input via one or more buttons, switches, knobs, etc. Additionally, user interface 206 may include a display configured to display information and one or more indicators, such as light indicators, audio indicators, etc., for conveying information and/or providing alerts regarding the operation of pump 100.

Pump 100 may be designed to be insertable into a patient's body, e.g., into a left ventricle of the heart, such as via an introducer system. Although some of the systems and/or methods disclosed herein are described for modulating a pump speed of a pump inserted into the left ventricle of a heart, it should be appreciated that the systems and/or methods described herein may also be applied to other types of ventricular support systems, such as a ventricular support system inserted into the right ventricle of the heart. In one aspect, housing 104, rotor 108, and outflow tube 106 may be radially compressible to enable pump 100 to achieve a relatively small outer diameter of, for example, 9 Fr (3 mm) during insertion. When pump 100 is inserted into the patient, e.g., into a left ventricle, handle 130 and motor 150 may remain disposed outside the patient. As will be appreciated, in other embodiments, the motor of the pump system may be disposed inside the patient upon insertion. During operation, motor 150 is controlled by processor(s) 204 to drive rotation of drive shaft 114 and rotor 108 to convey blood from inlet 116 to outlet 118. It is to be appreciated that rotor 108 may be rotated by motor 150 in reverse to convey blood in the opposite direction (in this case, the openings of 118 form the inlet and the openings of 116 form the outlet). In one aspect, pump 100 may be configured to be used for weeks to months to years to support the heart function of a patient with chronic heart failure, though it should be understood that the technology described herein is not limited to any particular types of procedures and/or use durations.

As described herein, the operation (e.g., speed) of conventional MCS devices are primarily manually configured to meet the physiological demands of the patient in the acute setting. When setting the operation of such devices, improvement in cardiac function over a longer period of time is typically not taken into consideration. Because MCS devices are typically configured to maintain acute physiological function, few patients currently recover from chronic heart failure while being supported with an MCS device. Some embodiments of the technology described herein are configured to identify and track improvement in cardiac function over time and may modulate the operation of the MCS device to facilitate the possibility of native heart recovery while also meeting acute physiological needs of the patient.

Figure 2:
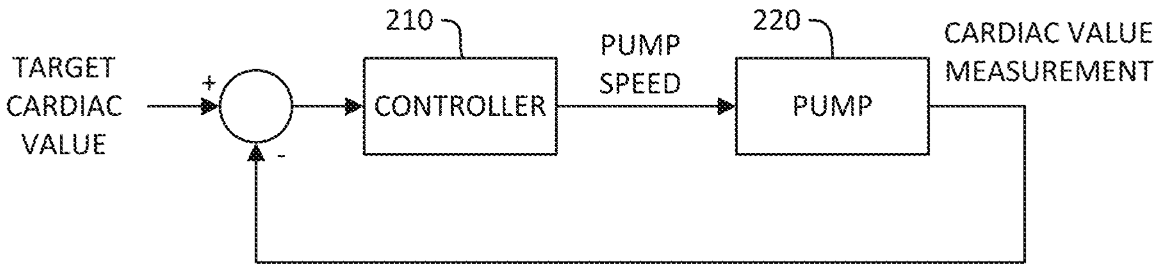
FIG. 2 illustrates a process for modulating operation of a pump system based on a measured cardiac value in accordance with some embodiments of the present technology.

FIG. 2 schematically illustrates a process for modulating the pump speed of an MCS device based on monitoring of a cardiac value associated with operation of the MCS device in accordance with some embodiments. In one example, the monitored cardiac value may correspond to left ventricular systolic pressure (LVSP). As shown in FIG. 2, a target cardiac value (e.g., a target LVSP value) may be compared to a measured cardiac value (e.g., a measured LVSP value) determined based, at least in part, on output from the MCS device. Based on a comparison of the target and the measured cardiac values, a controller 210 of the MCS device may be configured to adjust the speed of the pump 220 to improve the performance of the MCS device according to a patient's requirements. For instance, if the measured cardiac value is less than the target cardiac value, the controller may be configured to increase (or alternatively decrease) the speed of the pump in an attempt to align the measured cardiac value with the target cardiac value. In this way, the speed of the pump may be continuously or periodically modulated to achieve a particular cardiac performance objective.

Figure 3:
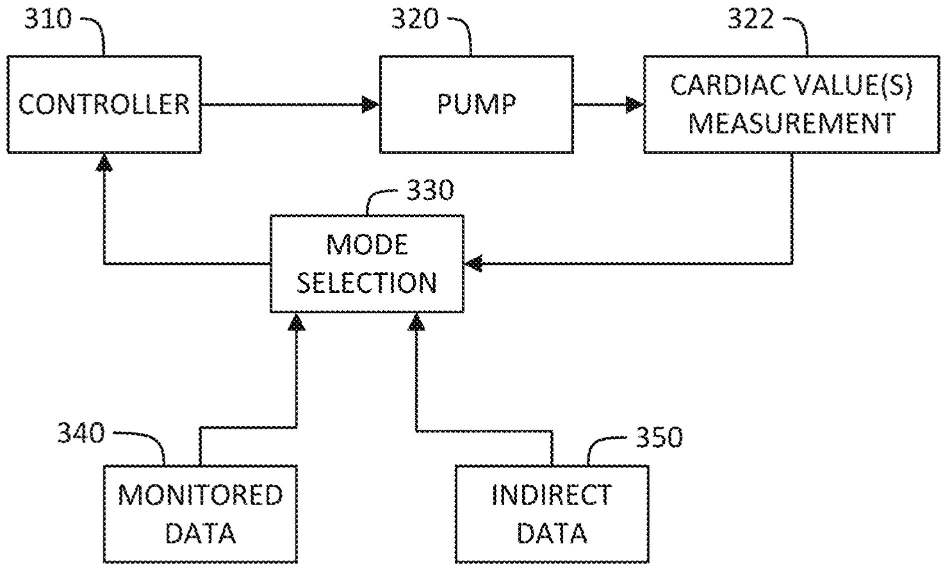
FIG. 3 illustrates a process for modulating operation of a pump system configured to operate in a plurality of modes in accordance with some embodiments of the present technology.

The inventors have recognized and appreciated that it may be advantageous to take into consideration multiple inputs when determining how to modulate operation of an MCS device when used to support a patient over a longer period of time (e.g., weeks to months to years). FIG. 3 illustrates a process for modulating operation of a blood pump of an MCS device in response to multiple inputs in accordance with some embodiments. Similar to the process shown in FIG. 2, in the example of FIG. 3, a controller 310 of an MCS device may be configured to control an operation (e.g., a speed) of a pump 320 of the MCS device based, at least in part, on an input signal provided to the controller 310. However, rather than monitoring a single cardiac value as described in FIG. 2, in the example of FIG. 3, the input signal is provided to controller 310 from a mode selector 330, which receives multiple inputs including one or more cardiac values 322 obtained from pump 320 and/or another component of the MCS device, monitored data 340 measured using one more sensors separate from the MCS device, and indirect data 350 determined based on information associated with a physiological state of the patient. Although mode selector 330 is shown in FIG. 3 as a separate component, it should be appreciated that in some embodiments, mode selector 330 may be incorporated within controller 310. Additionally, although mode selector 330 is shown as receiving input from three sources, it should be appreciated that in some embodiments mode selector 330 may receive input from more than or fewer than three sources.

The one or more measured cardiac values 322 obtained from the MCS device may include, but are not limited to, left ventricular end-diastolic pressure (LVEDP), left ventricular end-diastolic volume (LVEDV), aortic pressure (AoP), aortic volume (AoV) opening, contractility, heart rate (HR), cardiac output (CO), contractility index (CI), stroke volume, dP/dt, and tau. The monitored data 340 may include, but is not limited to, various signal values from additional monitors (e.g., blood pressure (BP), wall tension, coronary flow, strain, muscle oxygenation, sympathetic nervous system (SNS) innervation, etc.). The indirect data 350 may include, but is not limited to, values for mitral regurgitation (MR), septum position, and an artificial intelligence/machine learning (AI/ML) assessment of heart function improvement over time.

In some embodiments, mode selector 330 may be configured to provide as input to controller 310, a selection of one of a plurality of modules (also referred to herein as "modes"), each of the modules specifying instructions to provide a type of MCS device support tailored for the patient's current physiological needs and/or native heart recovery goals. For example, in some embodiments, the plurality of modules may include a decompression module with control instructions for alleviating acute injury and fully (or partially) unloading the left ventricle without suction. The plurality of modules may also include a physiologic module configured to facilitate reverse cardiac remodeling that occurs with heart disease. The physiologic modules may include one or more submodules for particular physiological needs of the patient. For example, the submodules may include an exercise mode in which more MCS device support is needed, a sleep mode in which less MCS device support is needed, and a daily or "normal" mode in which an average amount of MCS device support is needed. By utilizing submodules to enable variation in the level of MCS device support needed when the device is operating according to the physiologic module, daily routines of the patient, which require different levels of MCS device support can be accommodated. In some embodiments, switching between different modules and/or sub-modules may be based, at least in part, on various inputs provided to the mode selector 330. For instance, one or more sensors may be used to determine when a patient wakes up, stands up, or is in some other physiologic state in which additional pump support would be helpful to support the patient's cardiac function. In such instances, the mode selector 330 may be configured to automatically switch to a different module or submodule that provides pump flow that aligns with the patient's current physiologic state. The plurality of modules may also include a weaning module, which reduces the MCS device support prior to explanting the MCS device. Within each of the plurality of modules, the speed of the pump and/or the type of support provided may be modulated.

FIG. 4 illustrates a chart describing various characteristics of three exemplary modes for controlling operation (e.g., speed) of an MCS device in accordance with some embodiments. The modes shown in FIG. 4 and described in more detail herein are a decompression mode, a physiologic mode, and a weaning mode. It should be appreciated however, that any suitable number and/or types of modes for controlling operation of an MCS device may be used, and embodiments are not limited in this respect.

As described herein, in some embodiments, the controller of an MCS device may be configured to operate in one of a plurality of modes based, at least in part, on a type and/or level of support needed by the patient in accordance with their current stage of treatment. Characteristics of operation which may differ across modes include, but are not limited to, the type of flow through the pump (e.g., continuous, pulsatile, or a combination of continuous and pulsatile), the stimulus and/or clinical target values which are monitored to determine the operating parameters (e.g., pump speed) when in the mode, and whether or not the mode includes one or more sub-modes in which within the mode the MCS device is configured to operate with different parameters. As discussed herein, in some embodiments the MCS device may transition between modes (or sub-modes) (e.g., either in response to user input or automatically without explicit user input) to facilitate recovery of native heart function.

In a decompression mode, the patient may need continuous/maximal support from the MCS device to address acute symptoms of heart failure. In such a mode, the controller of the MCS device may be instructed to provide continuous flow through the device with the aortic valve of the patient being closed most of the time. The goal of the decompression mode may be to provide volume unloading and/or optimized unloading of the left ventricle of the patient without suction. For instance, in some cases optimized unloading may be maximum unloading of the left ventricle based off physiological (e.g., cardiac) signals. Examples of the cardiac values that may be monitored and used to determine pump speed when in decompression mode include, but are not limited to, one or more of left ventricular end-diastolic pressure (LVEDP), left ventricular end-diastolic volume (LVEDV), left ventricular end-diastolic diameter (LVEDD), and septum position. It should be appreciated, however, that other cardiac values may additionally or alternatively be used to modulate operating parameters within decompression mode and/or to determine when to transition from decompression mode to another mode (e.g., physiologic mode), such cardiac values including, but not limited to those described herein.

In a physiologic mode, the patient may need less and/or different support from the MCS device than when the MCS device is operating in decompression mode. For example, the patient's native heart function may have recovered to a point where continuous flow and maximum unloading of the heart is no longer needed. In physiologic mode, the type of support provided by the MCS device may facilitate recovery of the patient's native heart function and/or may promote reversal of cardiac remodeling associated with heart disease. For example, in physiologic mode, the flow type may be pulsatile rather than continuous to more closely mimic the functioning of the native heart and the aortic valve may open every few cycles (e.g., every 5 cycles) to maximize unloading while permitting native valve function. The goal of the physiologic mode may be to accommodate physiological responses and support needs of the patient in their daily life, while encouraging the restoration of native heart function in the patient.

Flexibility to accommodate for different support needs when in the physiologic mode may be achieved in some embodiments by defining a set of sub-modes, which modulate the operation of the MCS device based on expected cardiac demands during different activities during a patient's day. For instance, when more MCS device support is expected to be required during exercise, the controller of the MCS device may be instructed to operate in an exercise mode, which adjusts the pump speed to maintain the target mean arterial pressure (MAP) above a particular threshold (e.g., greater than 75-80 mmHg). By contrast, when less MCS device support is expected to be required during sleep, the controller of the MCS device may be instructed to operate in a sleep mode, which slows the speed of the pump, thereby relying on the native heart function to provide the needed support. A daily or "normal" mode may provide an average level of support as the patient goes about their daily activities. Any suitable cardiac values may be monitored and used to determine operating parameters for the MCS device when the controller is instructed to be in physiologic mode, and the monitored cardiac values may differ depending on a particular sub-mode that is currently being implemented by the controller. Examples of the cardiac values that may be monitored and used to determine pump speed when in physiologic mode include, but are not limited to, one or more of Aortic pressure (AoP), aortic wall tension, and mean arterial pressure (MAP), as described herein for exercise mode. It should be appreciated, however, that other cardiac values may additionally or alternatively be used to modulate operating parameters within decompression mode and/or to determine when to transition from physiologic mode to another mode (e.g., weaning mode), such cardiac values including, but not limited to those described herein.

In a weaning mode, the patient's native heart function may have recovered to a point where it may be possible to transition toward explant of the MCS device. In such a weaning mode, the speed of the pump may be gradually reduced to facilitate the weaning process. In weaning mode, the flow type may be pulsatile, continuous, or a combination of pulsatile and continuous, and may be driven, at least in part, on values associated with the native heart function of the patient. In the weaning mode, it is expected that the aortic valve of the patient will be open most of the time to transition the patient's heart away from reliance on the MCS device to provide cardiac support. Any suitable cardiac values may be monitored and used to determine operating parameters for the MCS device when the controller is instructed to be in weaning mode. Examples of the cardiac values that may be monitored and used to determine pump speed when in weaning mode include, but are not limited to, one or more of native cardiac output (CO) or cardiac index (CI), native stroke volume, and ejection fraction (EF). It should be appreciated, however, that other cardiac values may additionally or alternatively be used including, but not limited to those described herein.

As the patient recovers native heart function during chronic use of an MCS device, the controller of the MCS device may be instructed to transition between different operating modes of the device to facilitate native heart function recovery and/or reverse cardiac remodeling that occurs in heart disease. The timeline of transition between different modes may be patient specific to optimize the level and/or type of support being provided by the MCS device according to patient specific metrics regarding their native heart function.

Figure 5:
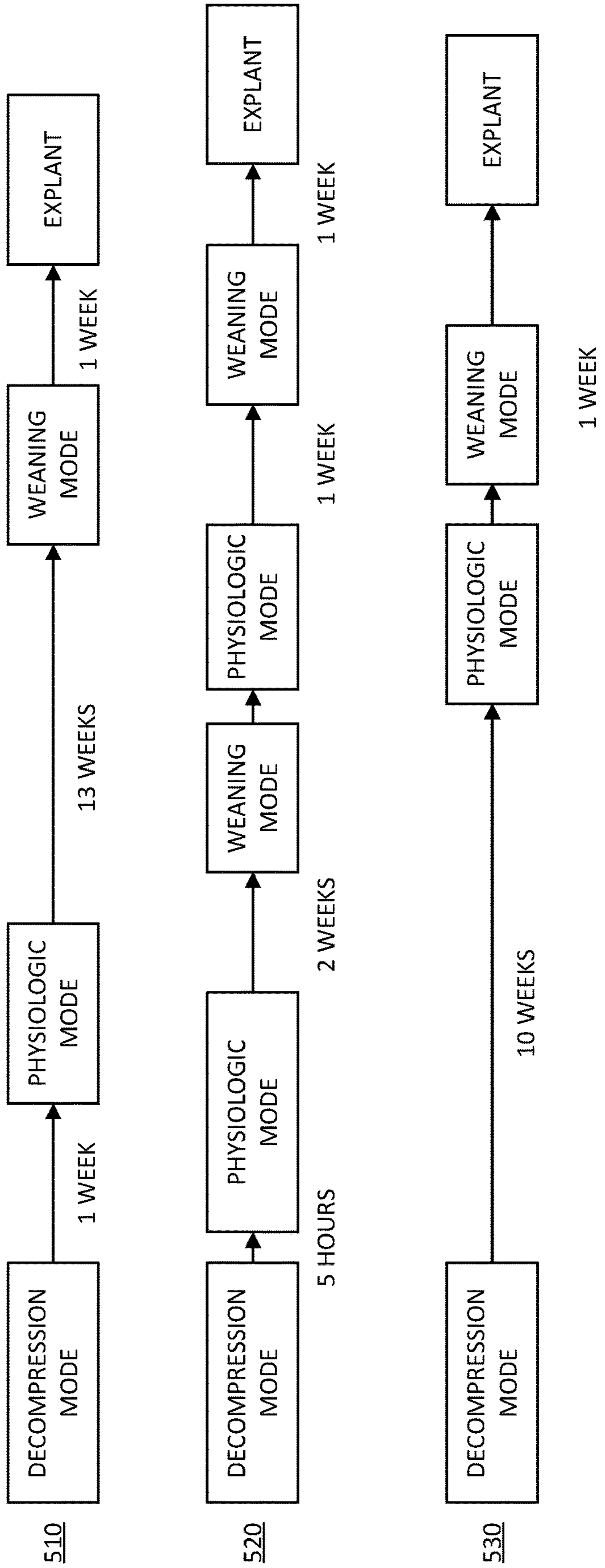
FIG. 5 illustrates a plurality of timelines for transitioning operation of a pump system of an MCS between different modes in accordance with some embodiments of the present technology.

FIG. 5 schematically illustrates three exemplary timelines (510, 520, 530) for three different patients transitioning between different operating modules/modes of an MCS device in accordance with some embodiments. In each of the illustrated timelines, the initial mode is decompression mode, in which the MCS device is controlled to provide maximal unloading of the heart after the MCS device is implanted in the patient.

As illustrated in both timeline 510 and timeline 530, the modes of the MCS device may be transitioned from decompression mode to physiologic mode to weaning mode, though at different times. In timeline 510, the transition between decompression mode and physiologic mode occurs within one week of starting decompression mode. By contrast, the transition between decompression mode and physiologic mode in timeline 530 occurs after a longer period of time (e.g., 10 weeks). As discussed herein, the transition between decompression mode and physiologic mode may be guided based, at least in part, on characteristics of the native heart function of the patient. In timeline 530, the patient may have had more severe heart disease in which the native functioning of the patient's heart prior to MCS device implantation was poor and thus longer support in the decompression mode may have been required compared to the patient in timeline 510, which may have had a less severe form of heart disease. Other reasons for delaying the transition from decompression mode to physiologic mode in timeline 530 relative to timeline 510 are also possible. In timeline 510, the operation of the MCS device remains in physiologic mode for 13 weeks prior to transitioning to weaning mode, where it remains for one week prior to explant of the MCS device. In timeline 530, the operation of the MCS device remains in physiologic mode for a shorter period of time (1 week) prior to transitioning to weaning mode followed by explant of the MCS device.

Timeline 520 illustrates a different sequence of transitions between modes of operation of the MCS device compared to those shown in timelines 510 and 530. In timeline 520 the operation of the MCS device may be transitioned from decompression mode to physiologic mode, although after a shorter time (e.g., 5 hours) after implant of the MCS device. The MCS device remains in physiologic mode for 2 weeks after which a transition to weaning mode occurs, possibly with the expectation that explant of the MCS device will occur shortly thereafter. However, based on the monitored cardiac values of the patient, it may be determined that the patient would benefit from reverting operation of the MCS device to physiologic mode prior to explant. Accordingly, the operation of the MCS device is transitioned from weaning mode to physiologic mode, where it remains for 1 week prior to again transitioning to weaning mode followed by explant. Timeline 520 illustrates the flexibility of some embodiments to freely transition between different modes based on the monitored cardiac values associated with the patient to provided patient-specific care using an MCS device. For instance, although only a transition from weaning mode back to physiologic mode is shown in FIG. 5, in some embodiments, a transition from physiologic mode back to decompression mode may also be possible should the monitored cardiac values associated with the patient indicate that the patient would benefit from the additional MCS device support provided in decompression mode. The timelines shown in FIG. 5 and described herein are merely exemplary and other timelines, including timelines in which less than all of the possible modules/modes are present are also contemplated. For instance, in one possible timeline, operation of the MCS device may be transitioned directly from decompression mode to weaning mode without first transitioning to physiologic mode.

Figure 6:
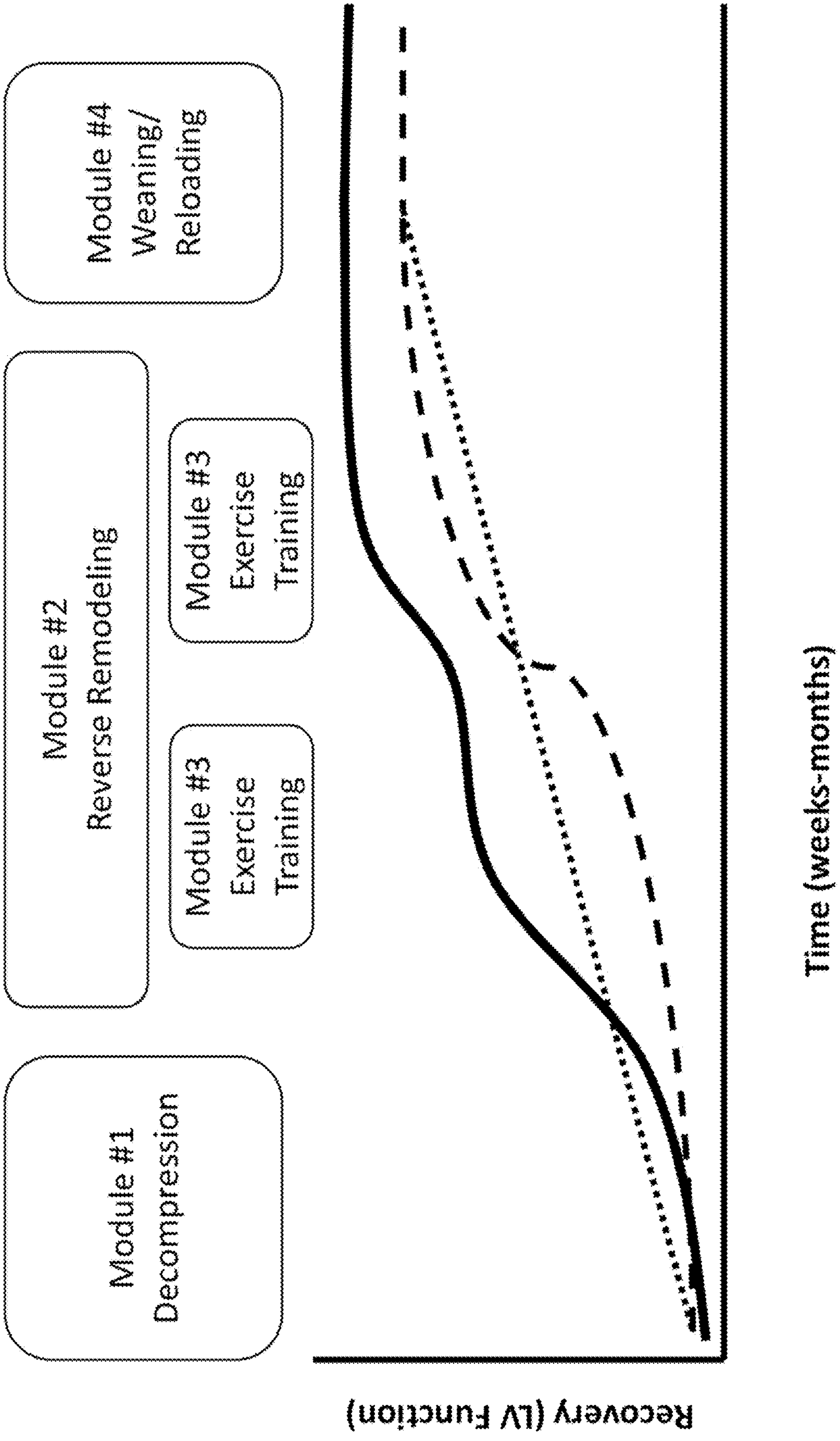
FIG. 6 schematically illustrates recovery of native heart function as a function of time when operation of a pump system of an MCS device is transitioned between different modes in accordance with some embodiments of the present technology.

FIG. 6 schematically shows how incorporating different operation modules/modes for an MCS device during chronic use of the device in accordance with the techniques described herein may facilitate recovery of native heart function in a patient. FIG. 6 shows the trajectory of recovery for native heart function (e.g., left ventricle function) for three different patients having an implanted MCS device for chronic use. As shown, each of the patients initially has poor native heart function, and as such, the MCS device is controlled to operate in a decompression mode, which provides optimized (e.g., maximum) unloading of the left ventricle. Over time, the native heart function of each of the patients begins to improve, though at different rates specific to the individual patient. As native heart function improves, the operation of the MCS device is transitioned to a different mode to facilitate further recovery of the patient's native heart function. It should be appreciated that module 2 ("Reverse Remodeling") shown in FIG. 6 may correspond to "physiologic mode" described in FIGS. 4 and 5, and module 3 ("Exercise Training") shown in FIG. 6 may correspond to the "exercise mode" sub-mode included as part of the physiologic mode described in FIG. 4.

As shown in FIG. 6, whereas each of the patients experienced modest recovery of native heart function while the MCS device was operated in decompression mode, recovery of native heart function while the MCS device was operated in reverse remodeling (e.g., physiologic mode) provided substantial improvement in native heart function, albeit at different rates. As native heart function recovers to a particular level, the operation of the MCS device may be transitioned to a weaning mode to prepare the patient for explant of the device, as described herein.

Figure 7:
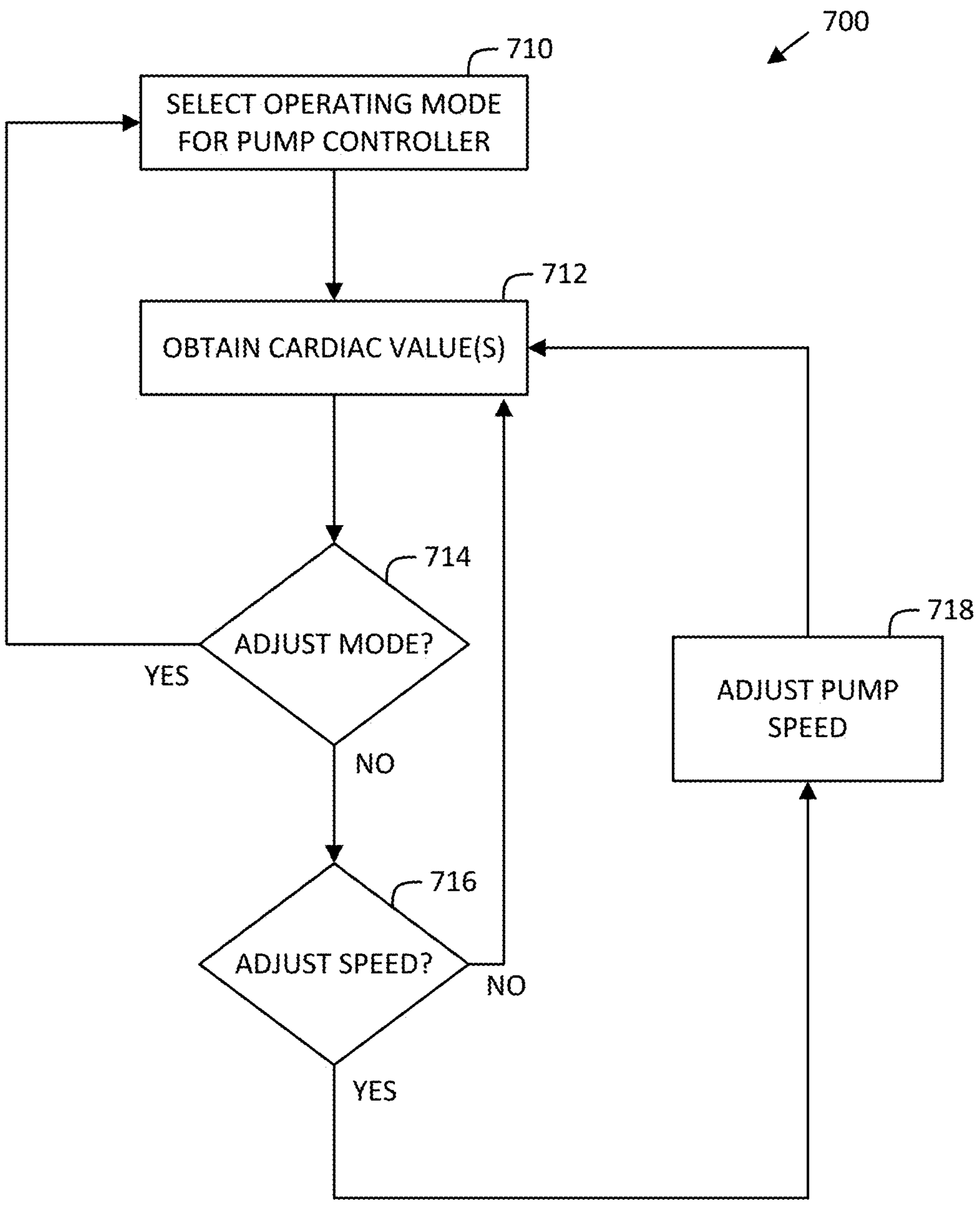
FIG. 7 illustrates a process for adjusting operation of a pump system of an MCS device in accordance with some embodiments of the present technology.

FIG. 7 illustrates a process 700 for modulating the operation of an MCS device during chronic use in a patient in accordance with some embodiments of the present disclosure. Process 700 begins in act 710, where an operation mode for the pump controller of an MCS device is selected. As described herein, the initial operation mode following implantation may be selected as a decompression mode in which optimized (e.g., maximum) unloading of the left ventricle is provided to ensure that the patient has adequate support from the MCS device to compensate for relatively weak native heart function. Process 700 may then proceed to act 712, where one or more cardiac values associated with the patient in which the MCS device is implanted are obtained. As described herein the obtained cardiac values may include values obtained directly from the MCS device, values obtained directly from one or more sensors external to the MCS device, and/or values obtained indirectly (e.g., from one or more models or algorithms) from sensor data associated with the patient. In some embodiments, a request may be provided to one or more sensors which may, in turn provide the value(s). In other embodiments, the obtained values(s) may be received without issuance of a request. In yet further embodiments, at least some of the values may be obtained in response to a request, whereas other values may be obtained without issuance of a request.

Process 700 may then proceed to act 714, where it is determined based, at least in part, on the obtained cardiac values(s) whether to adjust the operating mode of the MCS device. As described herein, the decision to transition the operating mode of the MCS device from one mode (e.g., decompression mode) to another mode (e.g., physiologic mode) may be based, at least in part, on a current recovery status of the patient's native heart function. The recovery status of the patient's native heart function may be determined based, at least in part, on the cardiac value(s) obtained in act 712. If it is determined in act 714 that the operating mode of the MCS device should be adjusted, process 700 returns to act 710, where a new operating mode for the pump controller of the MCS device is selected. The new operating mode may be, for example, a physiologic mode, a weaning mode, or a sub-mode of the currently selected mode (e.g., an exercise sub-mode of the physiologic mode).

If it is determined in act 714, that the operating mode of the MCS device should not be adjusted, process 700 proceeds to act 716, where it is determined whether the pump speed should be adjusted within the currently selected operating mode. If it is determined in act 716 that the pump speed does not need to be adjusted, process 700 returns to act 712 were the cardiac value(s) are again obtained. If it is determined in act 716, process 700 proceeds to act 718, where the pump speed is adjusted. For instance, the pump speed may be adjusted based, at least in part, on one or more of the cardiac value(s) obtained in act 712 to maintain a particular amount of desired MCS device support for the patient. In some embodiments, the pump speed may be adjusted based on a sub-mode (e.g., an exercise mode) within the currently selected operating mode.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. A method of controlling operation of a mechanical circulatory support (MCS) device to facilitate recovery of native heart function in a patient within which the MCS device is implanted, the method comprising:
- controlling a pump of the MCS device to operate in a first mode according to a first physiological need of the patient, wherein the first mode includes a first pump speed and a first pump timing, wherein the pump of the MCS device includes an inlet arranged in a first chamber of a heart of the patient and an outlet arranged in a second chamber of the heart of the patient, the pump configured to pump blood from the inlet to the outlet across at least one valve in the heart of the patient;
- obtaining one or more first cardiac values associated with the patient during operation of the MCS device;
- determining, based at least in part, on the obtained one or more first cardiac values, a second physiological need of the patient, wherein the second physiological need of the patient is different from the first physiological need of the patient; and
- controlling the pump of the MCS device to operate in a second mode according to the second physiological need of the patient, wherein the second mode includes a second pump speed and a second pump timing, wherein the first pump speed is different than the second pump speed and/or the first pump timing is different from the second pump timing.

2. The method of claim 1, wherein the first mode is a physiologic mode and the second mode is a sub-mode of the physiologic mode.

3. The method of claim 1, wherein
- the first mode includes first operating parameters configured to operate the pump with a first flow type, and
- the second mode includes second operating parameters configured to operate the pump with a second flow type different from the first flow type.

4. The method of claim 3, wherein the first flow type is continuous flow and the second flow type is a pulsatile flow.

5. The method of claim 1, wherein the first mode is a mode that provides optimized unloading of a left ventricle of the heart of the patient based on physiological signals.

6. The method of claim 5, wherein the second mode is a mode that modulates a speed of the pump of the MCS device based on physiological responses of the patient.

7. The method of claim 5, wherein the second mode is a mode that facilitates reverse remodeling of heart function in the patient.

8. The method of claim 5, wherein optimized unloading of the left ventricle comprises maximum unloading of the left ventricle.

9. The method of claim 1, further comprising:
- selecting a set of cardiac values to obtain based, at least in part, on the first mode,
- wherein obtaining one or more first cardiac values associated with the patient during operation of the MCS device comprises obtaining the one or more first cardiac values included in the set of cardiac values.

10. The method of claim 1, wherein the one or more first cardiac values include one or more values obtained from the pump of the MCS device.

11. The method of claim 1, further comprising:
- processing, with at least one machine learning model, information obtained from one or more sensors external to the MCS device to obtain the one or more first cardiac values.

12. The method of claim 1, wherein the one or more first cardiac values include one or more values obtained from the pump of the MCS device, one or more values obtained from one or more sensors external to the MCS device and one or more values obtained indirectly from information associated with one or more sensors associated with the MCS device and/or the one or more sensors external to the MCS device.

13. The method of claim 1, further comprising:
- determining, based at least in part, on the one or more first cardiac values to adjust a speed of the pump of the MCS device; and
- adjusting the speed of the pump of the MCS device when it is determined to adjust the speed of the pump and when it is not determined to transition operation of the MCS device to the second mode.

14. The method of claim 1, further comprising:
- obtaining one or more second cardiac values associated with the patient during operation of the MCS device in the second mode;
- determining, based at least in part, on the obtained one or more second cardiac values, a third physiological need of the patient, wherein the third physiological need of the patient is different from the second physiological need of the patient; and
- controlling the pump of the MCS device to operate in a third mode according to the third physiological need of the patient.

15. The method of claim 14, wherein the first mode is a decompression mode, the second mode is a physiologic mode and the third mode is a weaning mode.

16. The method of claim 14, further comprising:
- selecting a set of cardiac values to obtain based, at least in part, on the second mode,
- wherein obtaining one or more second cardiac values associated with the patient during operation of the MCS device in the second mode comprises obtaining the one or more second cardiac values included in the set of cardiac values.

17. The method of claim 1, wherein the MCS device is a left ventricular assist device (LVAD).

18. The method of claim 1, further comprising:
- receiving via a user interface, an instruction to transition operation of the MCS device to the second mode,
- wherein controlling the pump to operate in the second mode is performed in response to receiving the instruction.

19. A controller for a pump of a mechanical circulatory support (MCS) device, the controller comprising:
- at least one hardware processor configured to:
  - control the pump of the MCS device to operate in a first mode according to a first physiological need of a patient, wherein the first mode includes a first pump speed and a first pump timing, wherein the pump of the MCS device includes in inlet arranged in a first chamber of a heart of the patient and an outlet arranged in a second chamber of the heart of the patient, the pump configured to pump blood from the inlet to the outlet across at least one valve in the heart of the patient;

obtain one or more first cardiac values associated with the patient within which the MCS device is implanted, wherein the one or more first cardiac values are obtained during operation of the MCS device;

determine, based at least in part, on the obtained one or more first cardiac values, a second physiological need of the patient, wherein the second physiological need of the patient is different from the first physiological need of the patient; and control the pump of the MCS device to operate in a second mode according to the second physiological need of the patient, wherein the second mode includes a second pump speed and a second pump timing, wherein the first pump speed is different than the second pump speed and/or the first pump timing is different from the second pump timing.

20. A mechanical circulatory support (MCS) device, comprising:

a pump, wherein the pump includes an inlet arranged in a first chamber of a heart of a patient and an outlet arranged in a second chamber of the heart of the patient, the pump configured to pump blood from the inlet to the outlet across at least one valve in the heart of the patient; and a controller coupled to the pump, the controller comprising at least one hardware processor configured to:

control the pump to operate in a first mode according to a first physiological need of the patient, wherein the first mode includes a first pump speed and a first pump timing;

obtain one or more first cardiac values associated with the patient within which the MCS device is implanted, wherein the one or more first cardiac values are obtained during operation of the MCS device;

determine, based at least in part, on the obtained one or more first cardiac values, a second physiological need of the patient, wherein the second physiological need of the patient is different from the first physiological need of the patient; and control the pump to operate in a second mode according to the second physiological need of the patient, wherein the second mode includes a second pump speed and a second pump timing, wherein the first pump speed is different than the second pump speed and/or the first pump timing is different from the second pump timing.

* * * * *